United States Patent
Heggeness

(10) Patent No.: US 11,364,069 B2
(45) Date of Patent: Jun. 21, 2022

(54) DEVICE AND METHOD FOR ALLEVIATION OF PAIN

(71) Applicant: Michael Heggeness, Wichita, KS (US)

(72) Inventor: Michael Heggeness, Wichita, KS (US)

(73) Assignee: Michael Heggeness, Wichita, KS (US)

( * ) Notice: Subject to any disclaimer, the term of this patent is extended or adjusted under 35 U.S.C. 154(b) by 701 days.

(21) Appl. No.: 16/276,684

(22) Filed: Feb. 15, 2019

(65) Prior Publication Data

US 2019/0175252 A1 Jun. 13, 2019

Related U.S. Application Data

(62) Division of application No. 14/739,674, filed on Jun. 15, 2015, now abandoned.

(60) Provisional application No. 62/012,091, filed on Jun. 13, 2014.

(51) Int. Cl.
*A61B 18/14* (2006.01)
*A61B 18/00* (2006.01)
*A61B 90/00* (2016.01)

(52) U.S. Cl.
CPC ........ *A61B 18/148* (2013.01); *A61B 18/1477* (2013.01); *A61B 2018/00434* (2013.01); *A61B 2018/00577* (2013.01); *A61B 2018/00791* (2013.01); *A61B 2018/1425* (2013.01); *A61B 2018/1432* (2013.01); *A61B 2090/036* (2016.02)

(58) Field of Classification Search
CPC ............ A61B 18/148; A61B 2090/036; A61B 18/1477; A61B 2018/00434; A61B 2018/1425; A61B 2018/1432
See application file for complete search history.

(56) References Cited

U.S. PATENT DOCUMENTS

| | | | |
|---|---|---|---|
| 6,669,242 B2 | 12/2003 | Fountaine et al. | |
| 6,907,884 B2 | 6/2005 | Pellegrino et al. | |
| 7,749,218 B2 | 7/2010 | Pellegrino et al. | |
| 8,419,730 B2 | 4/2013 | Pellegrino et al. | |
| 8,425,507 B2 | 4/2013 | Pellegrino et al. | |
| 8,613,744 B2 | 12/2013 | Pellegrino et al. | |
| 8,623,014 B2 | 1/2014 | Pellegrino et al. | |
| 8,628,528 B2 | 1/2014 | Pellegrino et al. | |
| 9,282,993 B1* | 3/2016 | Cohen ................ | A61B 17/3421 |

(Continued)

OTHER PUBLICATIONS

Singh, Roop et al. 2011. Morphometric Measurements of Cadaveric Thoracic Spine in Indian Population and Its Clinical Applications. Asian spine journal. 5. 20-34. <https://www.researchgate.net/figure/Vertebral-body-dimensions-anterior-vertebral-body-height-posterior-vertebral-body_tbl3_50349060> (Year: 2011).*

(Continued)

*Primary Examiner* — Linda C Dvorak
*Assistant Examiner* — Ryan T Clark
(74) *Attorney, Agent, or Firm* — Hovey Williams LLP

(57) ABSTRACT

A target-treating system treats a target disposed within a bone of a patient. The system comprises a probe configured to be inserted into the bone and navigated therethrough toward the target. The probe comprises a shaft that includes a proximal end, a distal end, and a main body extending between and interconnecting the proximal end and the distal end. The distal end is configured to engage the target such that, upon activation of the probe, the target is treated.

24 Claims, 8 Drawing Sheets

(56) References Cited

U.S. PATENT DOCUMENTS

| | | | |
|---|---|---|---|
| 2001/0047167 A1* | 11/2001 | Heggeness | A61B 18/148 606/41 |
| 2009/0143782 A1* | 6/2009 | Levi | A61B 90/92 606/79 |
| 2012/0239050 A1* | 9/2012 | Linderman | A61B 17/8811 606/94 |
| 2014/0324051 A1 | 10/2014 | Pellegrino et al. | |
| 2014/0336667 A1 | 11/2014 | Pellegrino et al. | |
| 2015/0359586 A1 | 12/2015 | Heggeness | |

OTHER PUBLICATIONS

Becker, et al., "Ablation of the basivertebral nerve for treatment of back pain: a clinical study", The Spine Journal 17 (2017) 218-223.

Fischgrund, et al., "Intraosseous basivertebral nerve ablation for the treatment of chronic low back pain: a prospective randomized double-blind sham-controlled multi-center study", European Spine Journal (2018) 27:1146-1156.

Khalil, et al., "A prospective, randomized, multicenter study of intraosseous basivertebral nerve ablation for the treatment of chronic low back pain", The Spine Journal 19 (2019) 1620-1632.

Yeh, et al., "Compressive loading at the end plate directly regulates flow and deformation of the basivertebral vein: an analytical study," Journal of Orthopaedic Surgery and Research, vol. 1, issue 18, 2006, 6 pages.

Heggeness, et al., "P38. An electron microscopic study of nerves within the human vertebral body," The Spine Journal, vol. 5, 2005, pp. 127S-128S.

Heggeness, et al., "Ablation of the Basivertebral Nerve for the Treatment of Back Pain: A Pilot Clinical Study," The Spine Journal, vol. 11, issue 10, pp. 65S-66S.

Antonacci, et al., "A Histologic Study of Fractured Human Vertebral Bodies," Journal of Spinal Disorders & Techniques, vol. 15, issue 2, Apr. 2002, pp. 118-126 (abstract).

Fras, et al., "Substance P-containing nerves within the human vertebral body: an immunohistochemical study of the basivertebral nerve," The Spine Journal, vol. 3, 2003, pp. 63-67.

Heggeness, et al., "Discography Causes End Plate Deflection," The Spine Journal, vol. 18, issue 8, Jun. 15, 1993, 1 page (abstract).

Antonacci, et al., "Innervation of the human vertebral body: a histologic study," Journal of Spinal Disorders & Techniques, vol. 11, issue 6, 1998, 1 page (abstract).

Barton, et al., "Intraosseous Innervation of the Human Patella A Histologic Study," The American Journal of Sports Medicine, vol. 35, issue 2, 2007, pp. 307-311.

Hipp, et al., "P59. The Neurovascular Supply of the Developing Vertebral Body: A MicroCT and Histologic Analysis of the Basivertebral Foramen, Nerve, and Vessels," The Spine Journal, vol. 9, 2009, p. 146S.

Becker, et al., "Ablation of the basivertebral nerve for treatment of back pain: a clinical study," The Spine Journal, Sep. 2016, 7 pages.

North American Spine Society, "Treatment of Chronic Low Back Pain via Ablation of the Basivertebral Nerve: Results of the SMART Trial", Nov. 2016, 1 page (abstract).

Office Action in co-pending U.S. Appl. No. 14/739,674, dated Mar. 9, 2017.

Office Action in co-pending U.S. Appl. No. 14/739,674, dated Oct. 5, 2017.

Office Action in co-pending U.S. Appl. No. 14/739,674, dated May 17, 2018.

Office Action in co-pending U.S. Appl. No. 14/739,674, dated Nov. 15, 2018.

\* cited by examiner

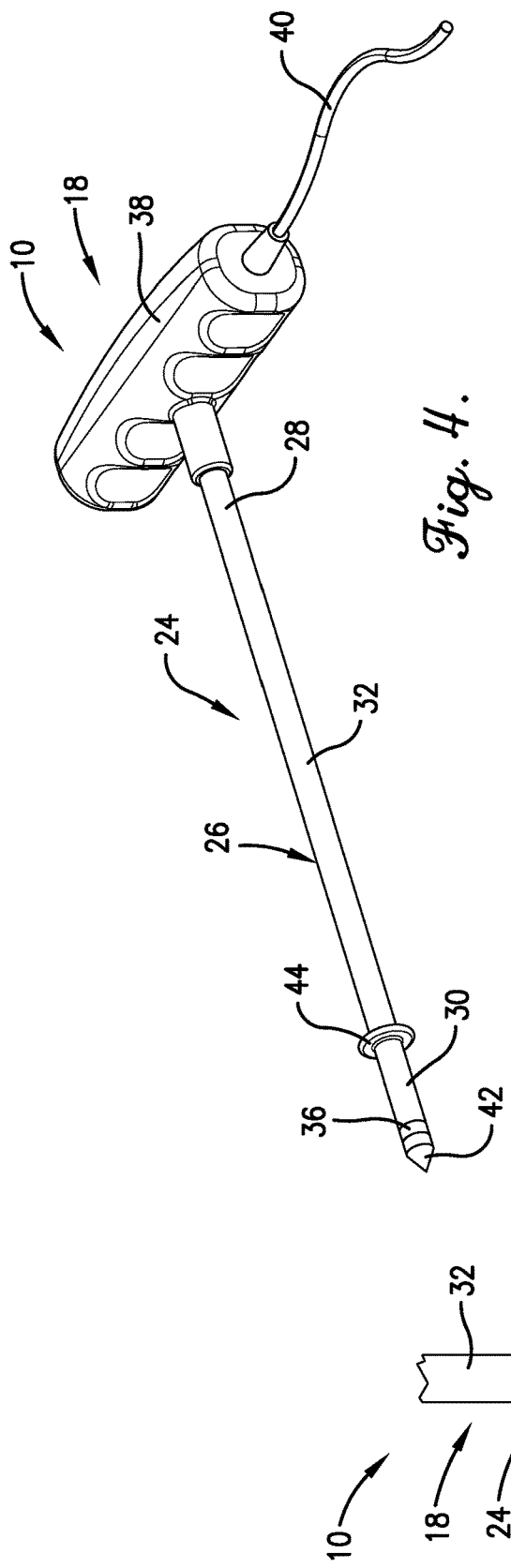
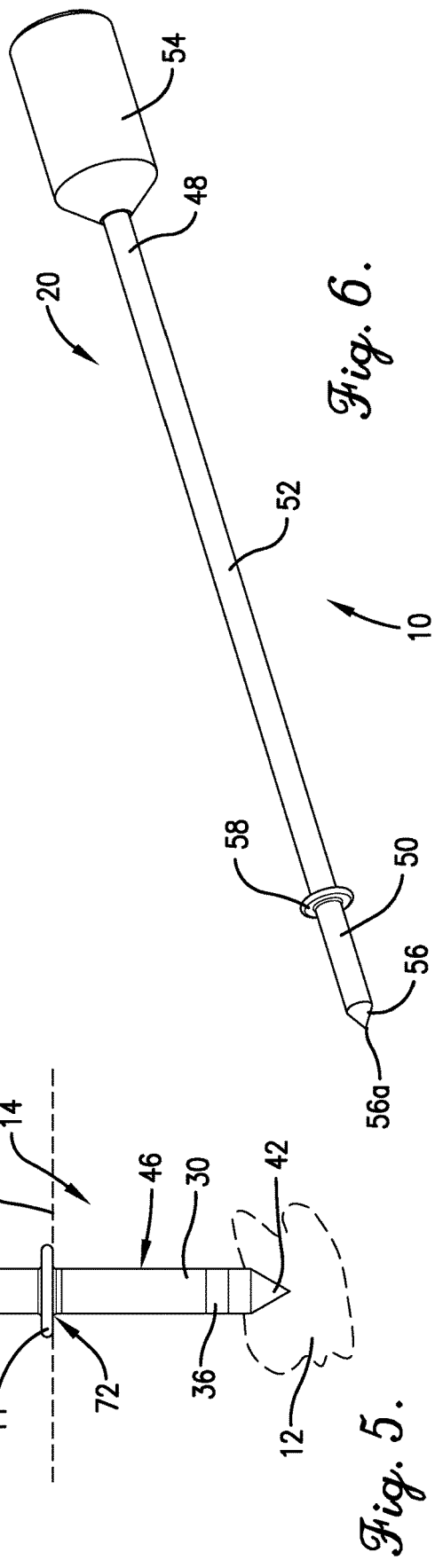
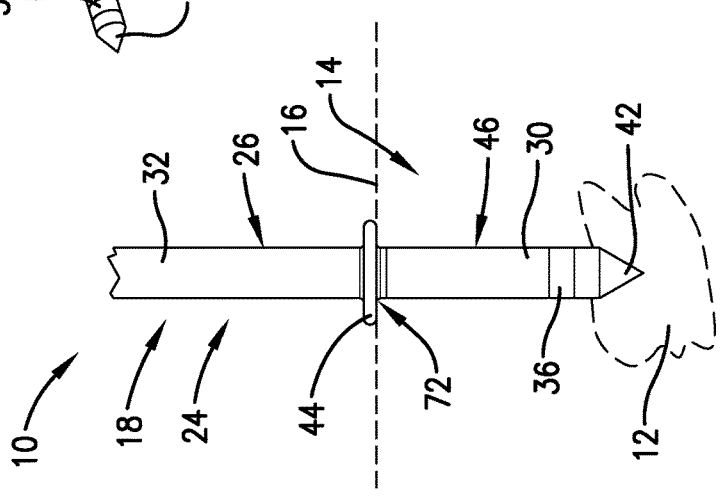

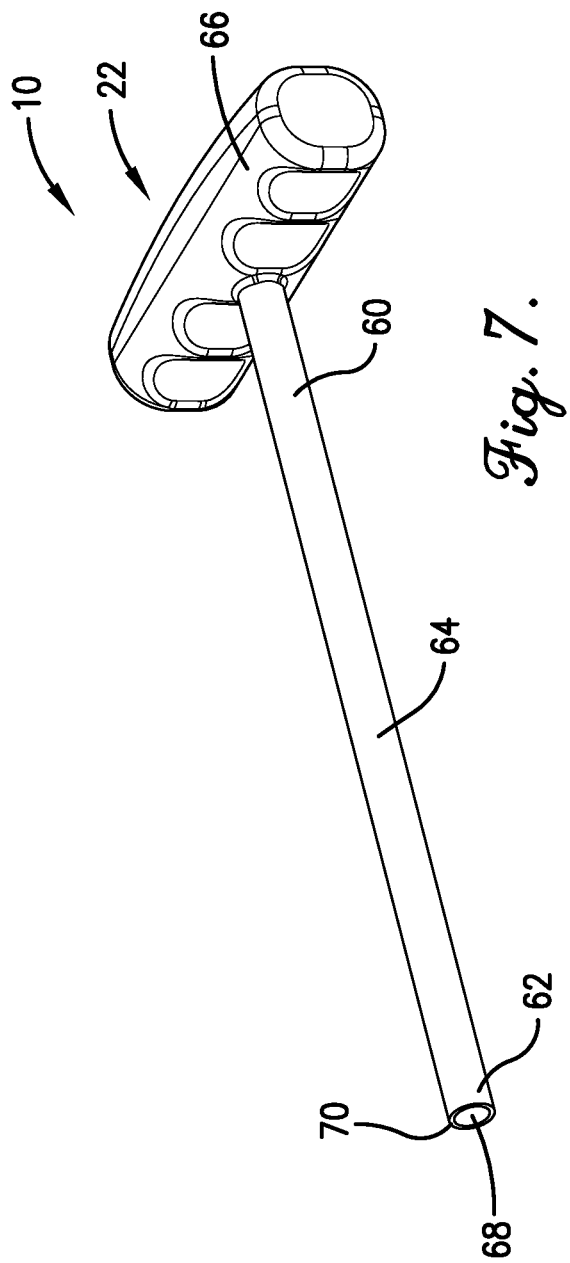
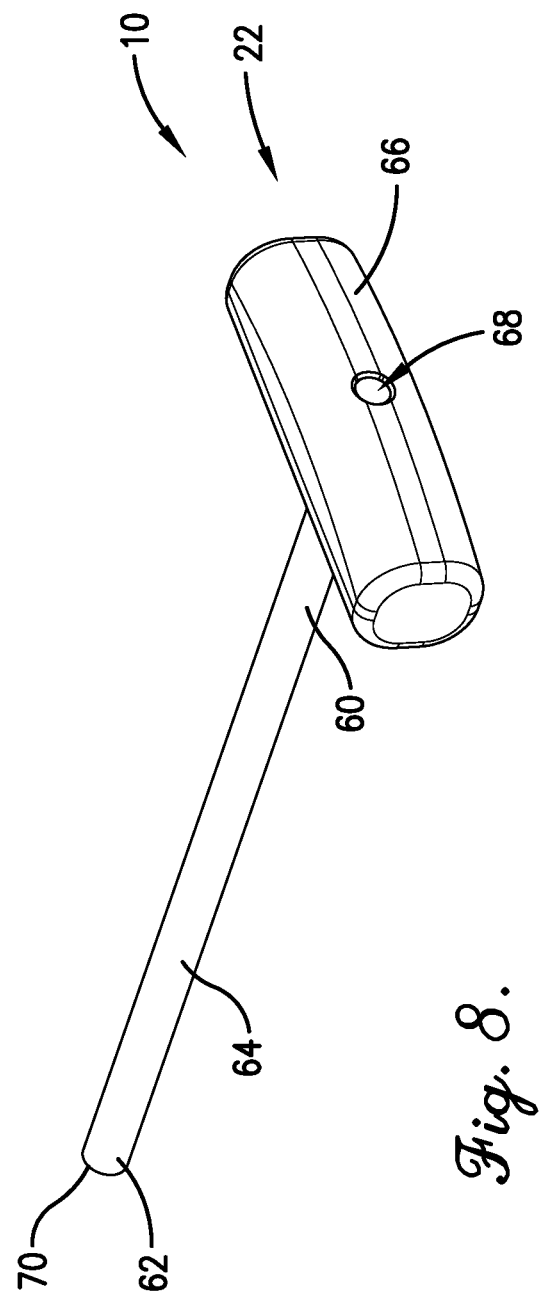

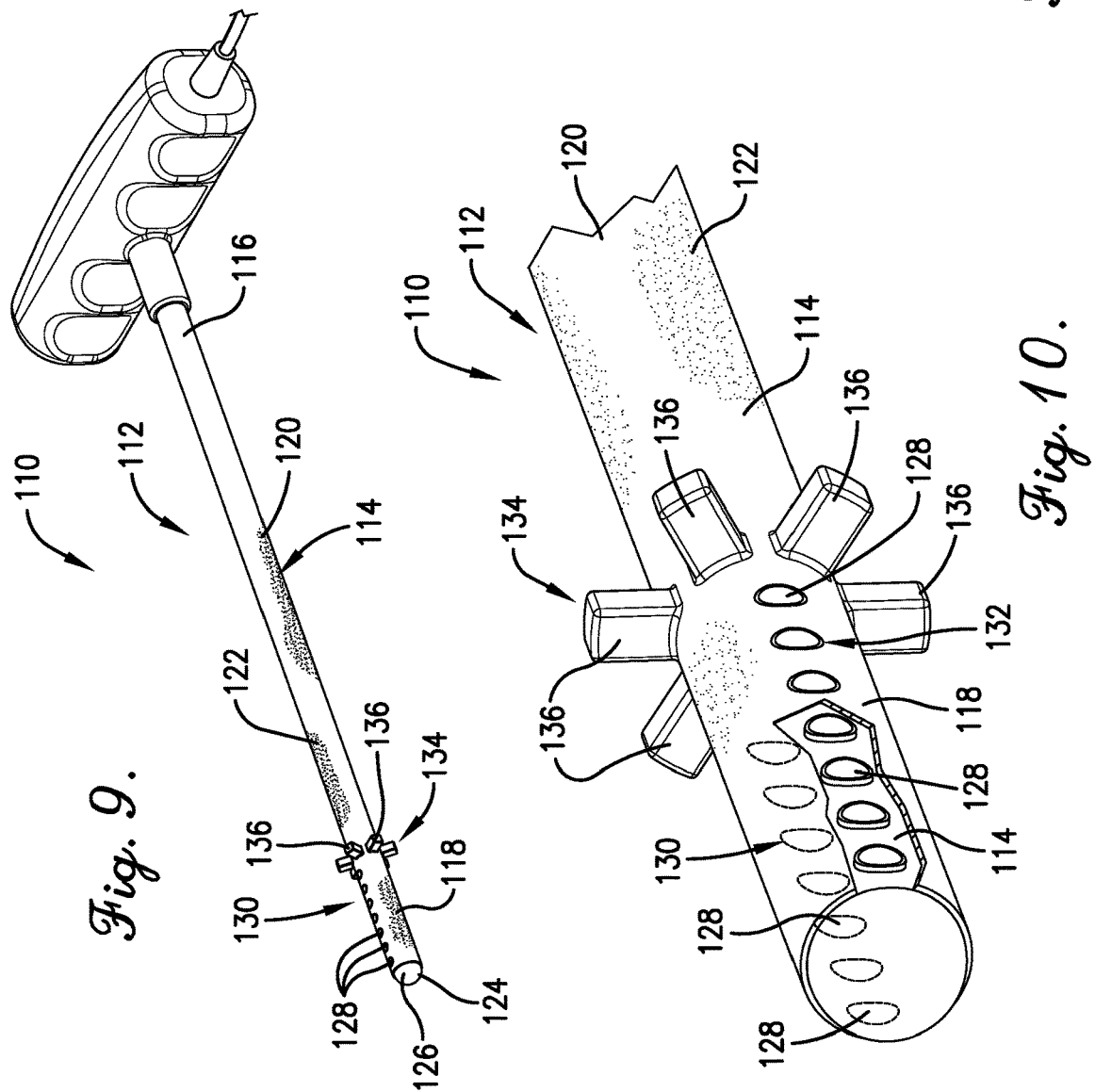

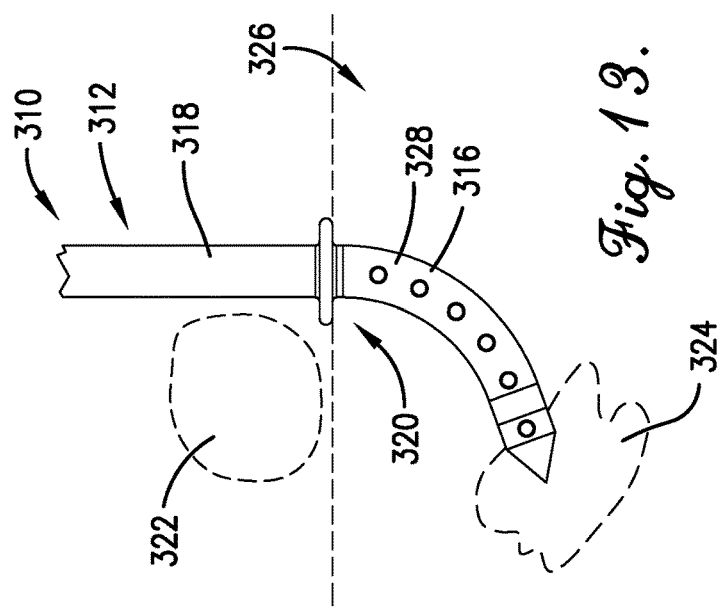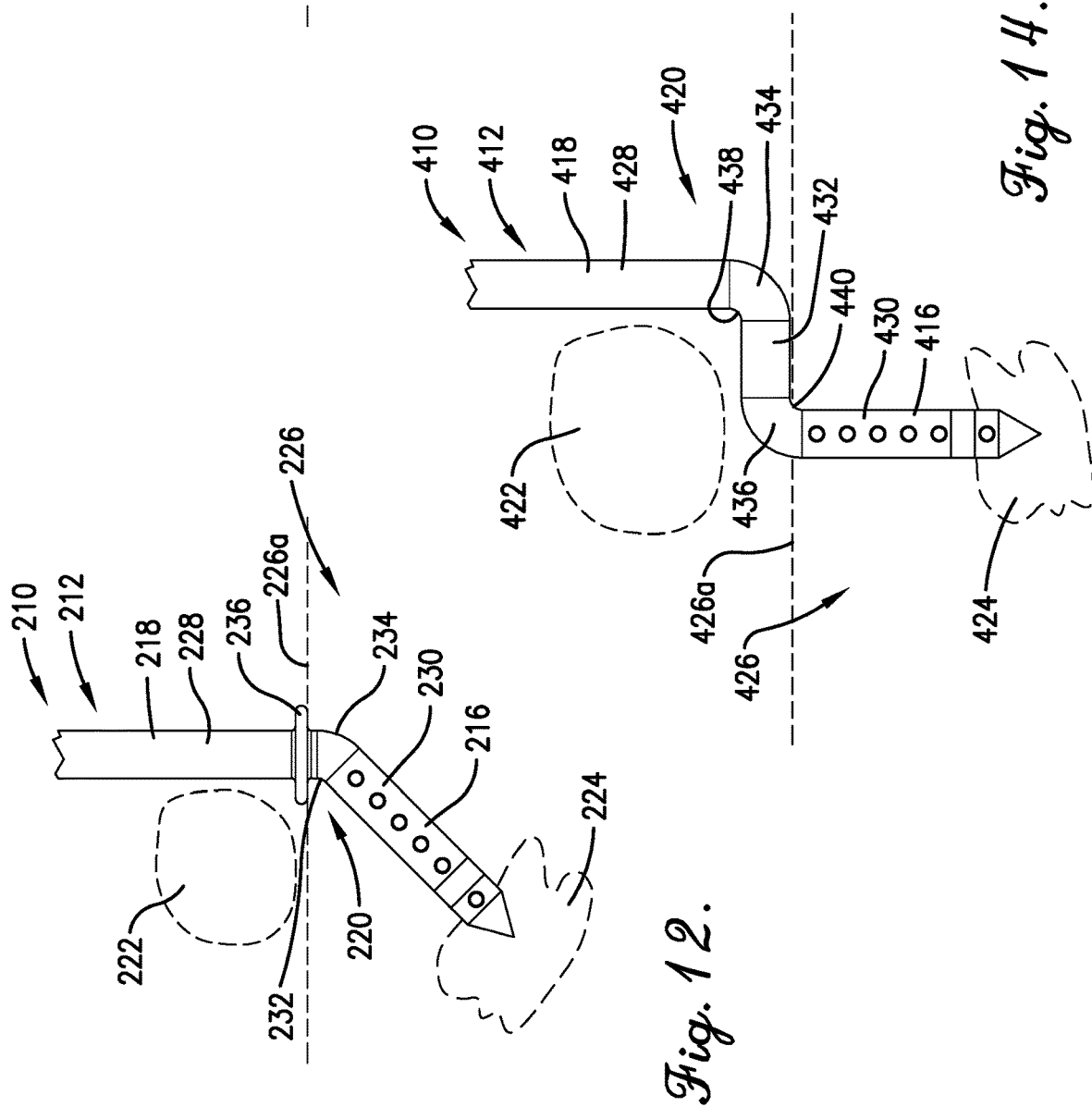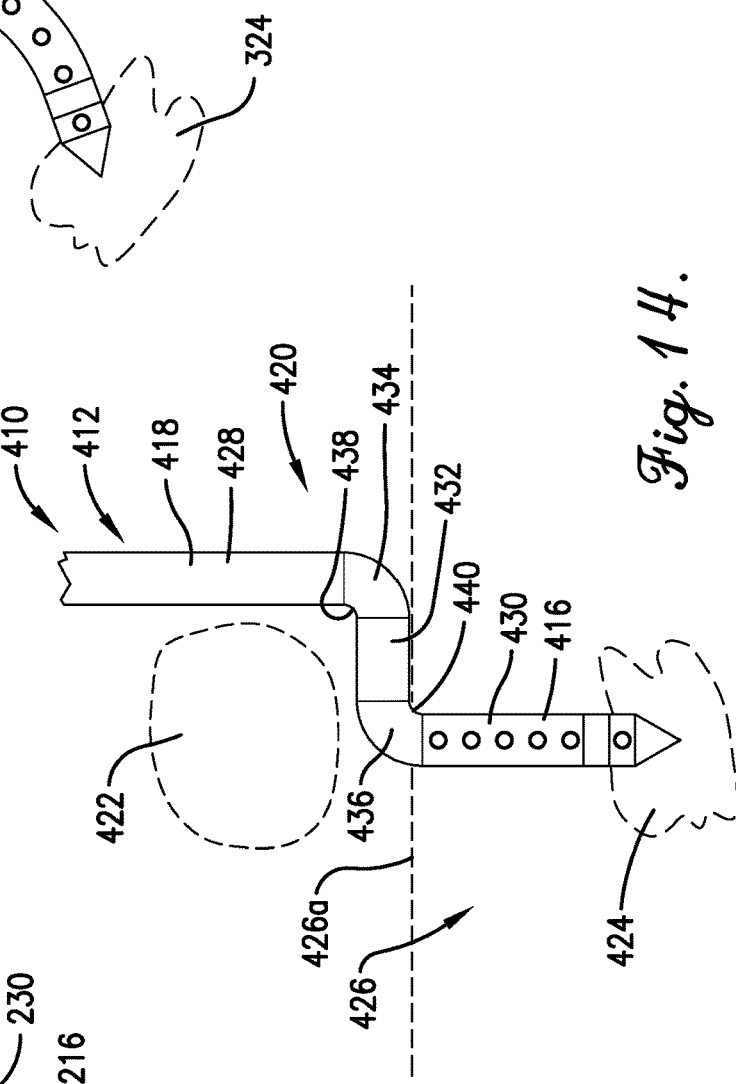

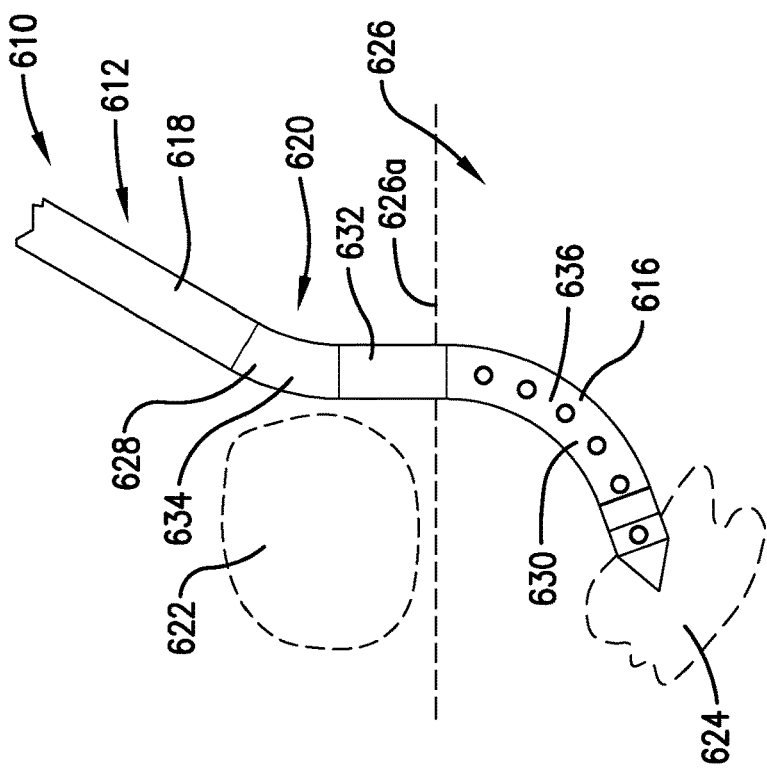
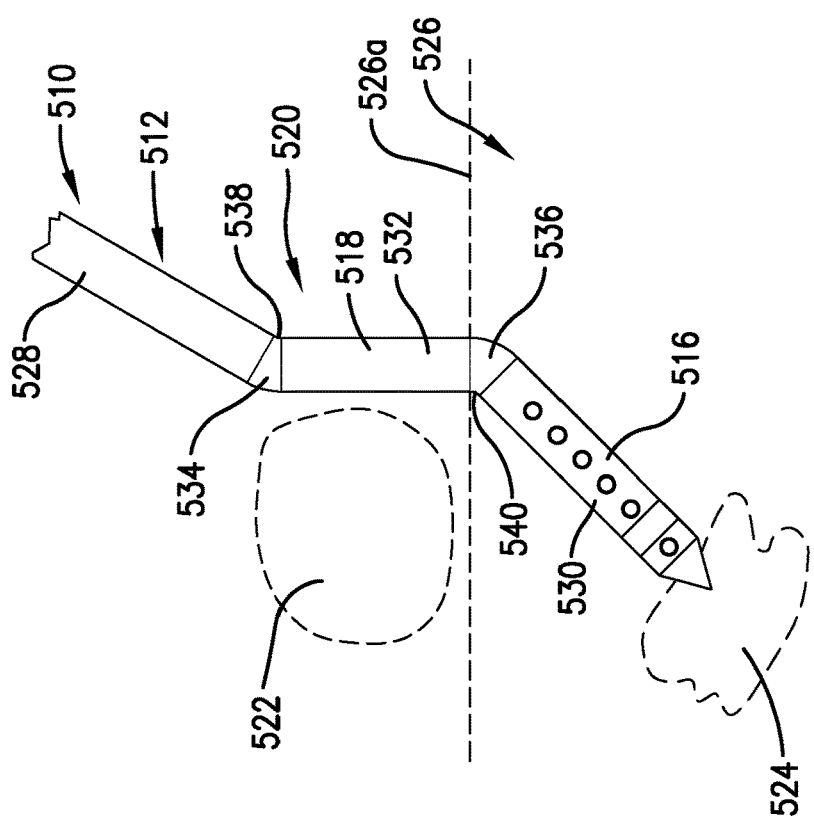

DEVICE AND METHOD FOR ALLEVIATION OF PAIN

CROSS-REFERENCE TO RELATED APPLICATIONS

The present application is a divisional application of U.S. patent application Ser. No. 14/739,674, filed Jun. 15, 2015, which claims the benefit of and priority from U.S. Provisional Patent Application No. 62/012,091, filed Jun. 13, 2014, the entire disclosure of each of which is hereby incorporated by reference herein. Furthermore, the present application is related to U.S. Pat. No. 6,699,242, filed Feb. 1, 2001, and U.S. Provisional Patent Application Ser. No. 60/179,959, filed Feb. 3, 2000, the entire disclosures of both of which are hereby incorporated by reference herein.

BACKGROUND OF THE INVENTION

1. Field of the Invention

The present invention relates generally to a device and method for treatment of a target structure. The device and method are particularly well-suited for surgical ablation of pain-producing structures within a bone (e.g., intraosseus nerves). For instance, as will be discussed in greater detail below, preferred embodiments of the present invention are well suited for use with methods for the treatment of back pain. More particularly, preferred embodiments of the present invention are well suited for use with methods of treatment of back pain that include ablation of a basivertebral nerve within a given vertebra.

FIG. 1 is a schematic illustration of an adult human H having a spine S. The spine S includes a plurality of vertebrae V defining a spinal canal SC (see FIG. 2). The spine S further includes a spinal cord (not shown) at least substantially received in the spinal canal SC. The vertebrae V provide structural protection to the spinal cord. Yet further, the spine S includes a plurality of intervertebral discs D alternately disposed between the vertebrae V.

Ligaments (not shown) provide support to the spine S. Furthermore, muscles (also not shown) are attached to the spine S primarily to enable movement thereof.

As shown in FIG. 1, the spine S includes thirty-three (33) individual vertebrae V defining five (5) spinal regions. From cranial to caudal, the five (5) spinal regions are the cervical spine CS, comprising seven (7) moveable vertebrae V; the thoracic spine TS, comprising twelve (12) moveable vertebrae V; the lumbar spine LS, comprising five (5) moveable vertebrae V; the sacrum SM, comprising five (5) fused vertebrae V; and the coccyx CX, comprising four (4) fused vertebrae V.

Although each vertebra V varies from the others, certain primary features are presented by each vertebra V. For instance, as shown in FIG. 2, each vertebra V includes a load-bearing body B, a vertebral arch A that in part defines a vertebral foramen F (and, in cooperation with other vertebral arches the spinal canal SC), and a plurality of processes P that provide attachment structure for muscles.

The spine S further includes a plurality of intraosseus nerves embedded in the vertebrae V. More particularly, the spine S includes a plurality of basivertebral nerves BVN extending through the vertebral bodies B. The basivertebral nerves BVN conduct pain signals from intraosseous sources. Therefore, ablation (i.e., removal or destruction by means including but not limited to cutting, abrading, evaporating, chemically or thermally modifying, etc.) of the basivertebral nerves BVN may lead to positive outcomes with respect to a patient's sensation of back pain.

Preferred embodiments of the present invention are also well suited for use with methods for the treatment of pain associated with the knee.

FIG. 3 illustrates a cross-sectional view of a human patella PT, illustrating the branching of an intraosseus patellar nerve PN therethrough. Similarly to the basivertebral nerves BVN of the spine S, the patellar nerves PN are thought to conduct pain signals. Ablation of the patellar nerves PN therefore may lead to positive outcomes with respect to a patient's sensation of knee pain.

Although additional bones are not illustrated or described in detail herein, it will be readily apparent to one of ordinary skill in the art that the present invention is at least generally applicable to the therapeutic treatment of nerves associated with any one or more of a variety of anatomical structures featuring intraosseus nerves, including but not limited to the pelvis, the femur, the fibula, the tibia, the humerus, the ulna, the radius, etc.

Furthermore, the present invention is not limited to use in treatment of humans, instead being at least generally applicable to veterinary use.

2. Discussion of the Prior Art

Those of ordinary skill in the art will appreciate that devices and methods for alleviating pain often result in thermal damage to and/or prolonged retraction of sensitive anatomic structures near or adjacent to the pain source itself and/or the access route to the pain source. Such sensitive structures include but are not limited to fluid-filled structures (e.g., vessels, ducts, or dura mater) and parts of the alimentary canal or lymphatic system.

Furthermore, methods of use of such devices are often limited exclusively to generally posterior approaches (i.e., entry from the posterior side) to the pain source due at least in part to obstructed generally anterior access.

SUMMARY

According to one aspect of the present invention, a method of ablating a nerve disposed within a vertebra of a patient is provided. The vertebra includes a main body and a plurality of processes. The main body of the vertebra presents a generally anterior face. The method comprises the steps of: (a) positioning a probe to circumvent a sensitive biological structure external to the vertebra, such that incidental damage by the probe to the sensitive biological structure is at least in part avoided during the course of said positioning; (b) inserting the probe into the generally anterior face of the main body of the vertebra in a generally anterior-to-posterior direction; (c) navigating the probe through the main body of the vertebra toward the nerve; (d) engaging the nerve with a distal end of the probe; and (e) activating the probe such that the nerve is ablated. The probe comprises a unitary shaft. The shaft includes a proximal end, the distal end, and a main body extending between and interconnecting the proximal end and the distal end. The proximal end, the distal end, and the main body of the shaft are integrally formed with one another. The main body of the shaft integrally forms an obstruction-avoidance portion that circumvents the sensitive biological structure during at least steps (a) and (e). The obstruction-avoidance portion comprises a rigid material such that the obstruction-avoidance portion maintains a single, constant shape during each of steps (a)-(e).

Among other things, a method as described above for ablating a nerve disposed within a vertebra of a patient enables precise, efficient, cost-effective treatment of associated pain while minimizing damage to a sensitive biological structure in the vicinity of the respective vertebra.

This summary is provided to introduce a selection of concepts in a simplified form. These concepts are further described below in the detailed description of the preferred embodiments. This summary is not intended to identify key features or essential features of the claimed subject matter, nor is it intended to be used to limit the scope of the claimed subject matter.

Various other aspects and advantages of the present invention will be apparent from the following detailed description of the preferred embodiments and the accompanying drawing figures.

BRIEF DESCRIPTION OF THE DRAWING FIGURES

A preferred embodiment of the present invention is described in detail below with reference to the attached drawing figures, wherein:

FIG. 4 is a perspective view of a probe assembly according to a first preferred embodiment of the present invention;

FIG. 5 is a front view of the probe assembly of FIG. 4 engaging an intraosseous target;

FIG. 6 is a perspective view of a trochar for use in cooperation with the probe of FIGS. 4 and 5;

FIG. 7 is perspective view of a sheath for use in cooperation with the probe of FIGS. 4 and 5 and the trochar of FIG. 6;

FIG. 8 is an alternative perspective view of the sheath of FIG. 7;

FIG. 9 is perspective view of a probe assembly according to a second preferred embodiment of the present invention;

FIG. 10 is an enlarged, fragmented perspective view of a portion of the probe assembly of FIG. 9, particularly illustrating the temperature sensors and electrically insulative coating;

FIG. 11 is a front view of the probe assembly of FIGS. 9 and 10 engaging an intraosseous target;

FIG. 12 is a front view of a probe according to a third preferred embodiment of the present invention, wherein the probe defines an obtuse angle and engages an intraosseus target;

FIG. 13 is a front view of a probe according to a fourth preferred embodiment of the present invention, wherein the probe defines a curve and engages an intraosseus target;

FIG. 14 is a front view of a probe according to a fifth preferred embodiment of the present invention, wherein the probe defines a pair of generally right-angle bends and engages an intraosseus target;

FIG. 15 is a front view of a probe according to a sixth preferred embodiment of the present invention, wherein the probe defines a pair of obtuse-angle bends and engages an intraosseus target;

Figure 17:
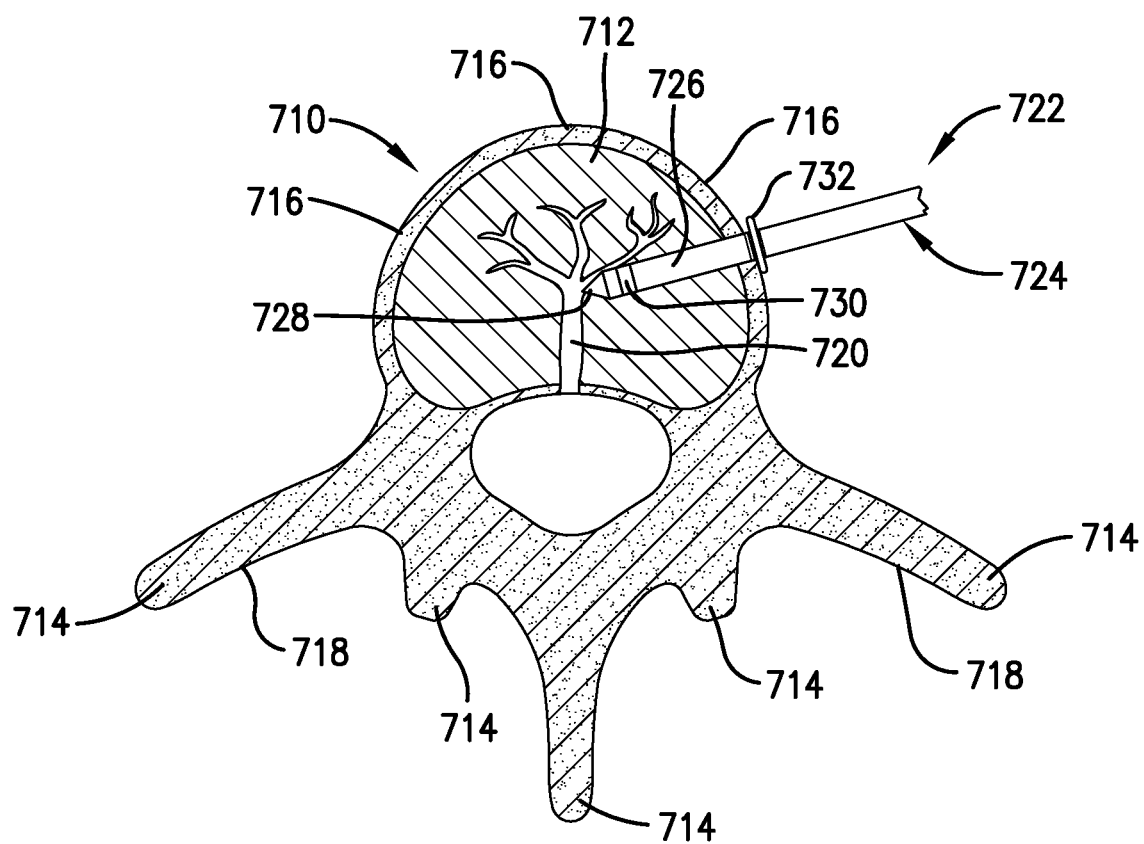

FIG. 16 is a front view of a probe according to a seventh preferred embodiment of the present invention, wherein the probe defines a pair of generally circularly extending bends and engages an intraosseus target; and FIG. 17 is a schematic cross-sectional top view of a vertebra, wherein a probe has been inserted into a generally anterior face thereof in a generally anterior-to-posterior direction to engage and treat the basivertebral nerve.

The drawing figures do not limit the present invention to the specific embodiments disclosed and described herein. The drawings are not necessarily to scale, emphasis instead being placed upon clearly illustrating the principles of the preferred embodiments.

DETAILED DESCRIPTION OF THE PREFERRED EMBODIMENTS

The present invention is susceptible of embodiment in many different forms. While the drawings illustrate, and the specification describes, certain preferred embodiments of the invention, it is to be understood that such disclosure is by way of example only. There is no intent to limit the principles of the present invention to the particular disclosed embodiments.

It is further noted that preferred embodiments of the present invention may in some instances be realized through a combination of features compatible for use together despite having been presented independently as part of separate embodiments in the below description and drawings.

Yet further, it is noted that relevant directional references (e.g., anterior, posterior, proximal, and distal, etc.) used herein should be understood in the context of standard anatomical orientation. Such directional references will be readily understood by those of ordinary skill in the art.

Figure 1:
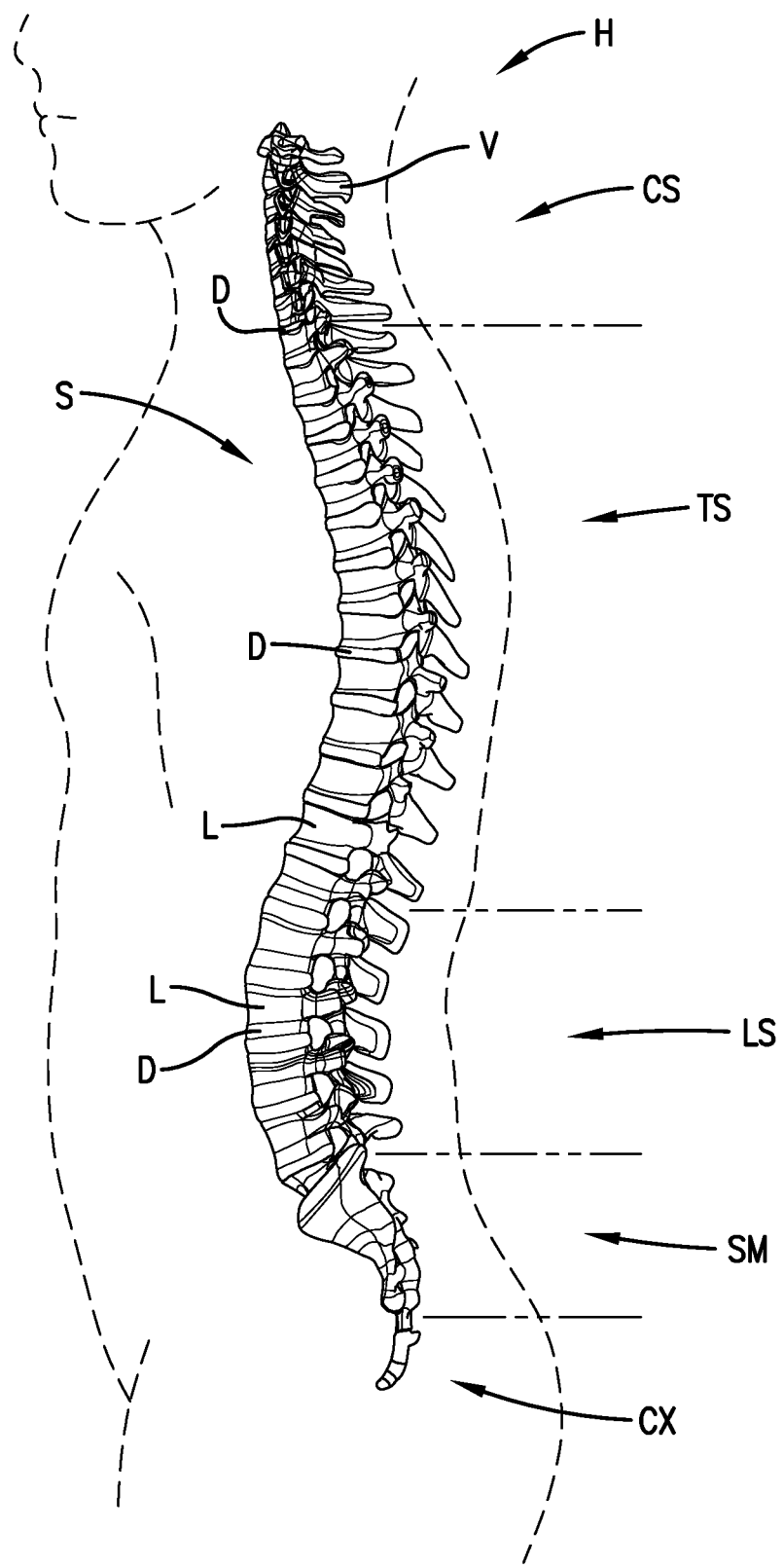
FIG. 1 is a schematic side view of a human spine.
Figure 2:
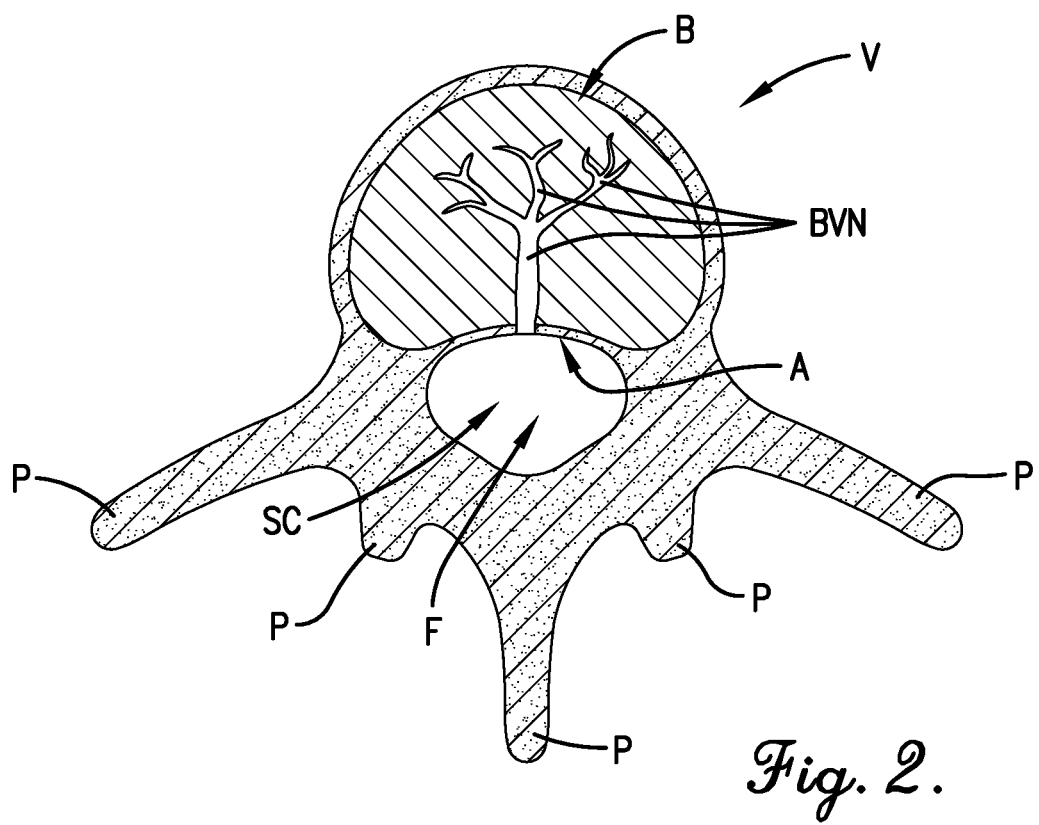
FIG. 2 is a schematic cross-sectional top view of a single vertebra of the human spine, particularly illustrating key anatomical features thereof, including a basivertebral nerve.
Figure 3:
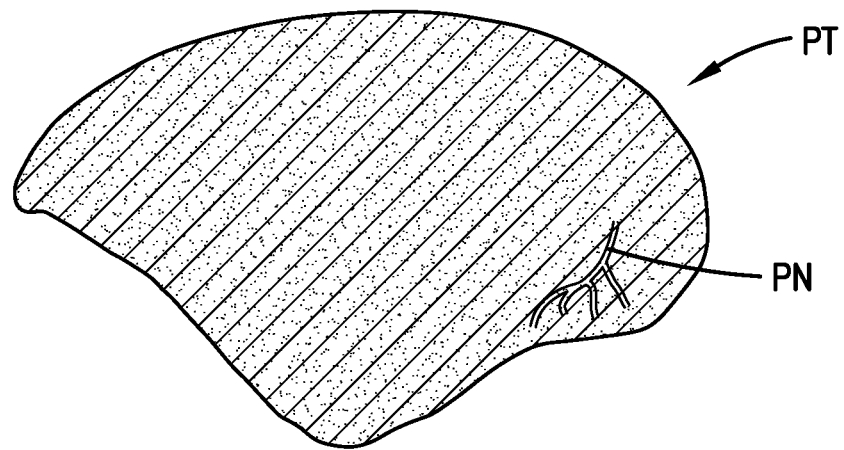
FIG. 3 is a schematic cross-sectional top view of a human patella, particularly illustrating the presence of a patellar nerve.

A first preferred target-treating system 10 is schematically illustrated in FIGS. 4-8. As will be discussed in greater detail below, the system 10 is preferably configured for therapeutic treatment of a target 12 disposed within a bone 14 defining an outer surface 16. The bone 14 is preferably a vertebra or patella (see, for instance, the vertebrae V of FIGS. 1 and 2 and the patella P of FIG. 3), and the target 12 is preferably an intraosseous nerve such as the basivertebral nerve BVN of FIG. 2 or the patellar nerve PN of FIG. 3. However, other applications, including but not limited to those associated with intraosseous pain sources, may fall within the scope of some aspects of the present invention. For instance, the target may be a nerve, a tumor, a vascular malformation, a stress fracture, a neurovascular structure, etc.

The system 10 preferably comprises a probe assembly 18, shown in FIGS. 4 and 5; a trochar 20, shown in FIG. 6, and a sheath 22, shown in FIGS. 7 and 8.

The probe assembly 18 preferably comprises a probe 24 that includes a shaft 26. The shaft 26 includes a proximal probe end 28, a distal probe end 30 spaced from the proximal probe end 28, and a main probe body 32 extending between and interconnecting the proximal probe end 28 and the distal probe end 30. Preferably, the shaft 26 extends generally longitudinally, such that the distal probe end 30 is spaced longitudinally from the proximal probe end 28.

As will be discussed in greater detail below, the probe 24 is configured to be inserted into the bone 14 and navigated therethrough toward the target 12. The distal probe end 30 is configured to engage the target 12 such that, upon activation of the probe 24, the target 12 is treated.

For instance, in the illustrated embodiment, the probe 24 is an electrocautery device configured to transmit electricity through the target 12 to ablate the target 12. More particularly, the proximal probe end 28 of the probe 24 is preferably operatively connected to an electrical source (not shown). The distal probe end 30 preferably comprises an electrically conductive material defining an electrode 36. Electricity travels from the electrical source (not shown) to the proximal probe end 28 and then to the distal probe end 30 and, more particularly, to the electrode 36.

The electrode 36 as illustrated in FIG. 4 is a bipolar electrode. However, as will be discussed in greater detail below, it is permissible according to some aspects of the present invention for the electrode to be a unipolar electrode.

Preferably, the main probe body 32 of the shaft 26 comprises an electrically conductive material, such that the electricity travels directly from the proximal probe end 28 to the distal probe end 30 (more specifically, the electrode 36) via the main probe body 32 of the shaft 26. It is permissible, however, for the probe assembly to alternatively include an electrically conductive wire or other conductive structure extending between the proximal end and the distal end or, more broadly, from the electrical source to the distal end. Such wire or structure might be routed along the shaft, through a lumen formed in the shaft, or in any other manner deemed suitable for the particular application.

The electrically conductive material may be any electrically conductive material known in the art, although it is preferable for such material to be particularly suited for surgical use. For instance, the electrically conductive material might suitably be surgical stainless steel or titanium.

The probe assembly 18 further preferably comprises a probe handle 38 to increase the ease of maneuverability of the probe 24.

Yet further, in keeping with the above-described electrocautery device embodiment, the probe assembly 18 of the first preferred embodiment includes wiring 40 extending to the ource of electricity (not shown).

Although the above-described electrocautery device embodiment is preferred, it is permissible according to some aspects of the present invention for the probe to be an alternate type of device capable of implementing a therapeutic effect on a target. For instance, the probe could alternatively be configured to deliver a coolant (e.g., liquid nitrogen, liquid air, liquid nitrous oxide, etc.), a chemical, or a medicinal/pharmaceutical agent (e.g., chemotherapy or radioactive substances, alcohols, acids, or solvents) to or near the target. In such a configuration, it will be readily apparent to one of ordinary skill in the art that the probe would require modification to enable transmission of the coolant, chemical, or agent therethrough (e.g., though provision of an internal fluid-transporting channel). Furthermore, the device would necessarily include or be attachable to means for storage of the coolant, chemical, or agent (e.g., a reservoir or syringe) and transfer thereof to the probe (e.g., a plunger or pump).

The probe also might alternatively comprise a laser, such as a fiber optic laser or other type of laser, or be configured to apply a direct thermal load.

In a preferred embodiment, as illustrated, the distal probe end 30 preferably includes a sharp tip 42. Such tip 42 preferably enables material removal, if necessary, in addition to enabling precise contact to be made between the tip 42 and the target 12 should a high degree of precision be advantageous in a given application. As discussed in greater detail below, however, the distal end may be alternatively configured to include a blunted or rounded tip. Yet further, the distal end might alternatively include a flat edge, a serrated edge (providing grip and stability, for instance) or any other geometry suitable for the particular application.

Preferably, the shaft 26 is at least substantially rigid. However, the shaft may alternatively be flexible in some embodiments of the device.

In the embodiment illustrated in FIG. 4, the main probe body 32 is at least substantially straight. As will be discussed in greater detail below, however, it is permissible and in some instances even preferable for the body to instead include one or more bends or turns.

The shaft 26 of the probe 24 preferably presents an at least substantially constant cross-sectional shape and size. More particularly, the shaft 26 preferably presents constant-diameter circular cross-sections. It is permissible according to some aspects of the present invention, however, for the shaft to present a non-circular cross-section. For instance, the shaft might be a in the form of a rectangular prism and present a square cross-section. Furthermore, it is permissible according to some aspects of the present invention for the cross-sectional shape to vary axially or longitudinally. Yet further, the cross-sectional dimensions may vary, either for a constant cross-sectional shape or for embodiments featuring multiple cross-sectional shapes.

In a preferred embodiment, the shaft 26 has a longitudinal dimension (i.e., a length) between about 20 cm and about 40 cm. More preferably, the shaft 26 has a longitudinal dimension of between about 25 cm and about 35 cm. Furthermore, the shaft 26 preferably has a maximum cross-sectional dimension (e.g., a diameter) of between about 1 mm to about 5 mm.

The probe 24 preferably includes a probe depth limiter 44 projecting generally laterally from the shaft 26 (i.e., in a manner non-parallel to the shaft 26). Most preferably, the probe depth limiter 44 projects generally orthogonally relative to a longitudinal axis of the shaft 26.

The probe depth limiter 44 preferably prevents over-insertion of the probe 24 into the bone 14. More particularly, the probe depth limiter 44 preferably engages the outer surface 16 of the bone 14 when the tip 42 has been embedded a maximum distance. The probe depth limiter 44 thus at least in part enables the avoidance of damage to biological tissues as a result of over-insertion.

The probe depth limiter 44 is preferably spaced a predetermined longitudinal distance from the distal probe end 30. More particularly, the probe depth limiter 44 is preferably spaced a distance between about 1 mm and about 35 mm from the distal probe end 30. More preferably, the probe depth limiter 44 is preferably spaced a distance between about 5 mm and about 30 mm from the distal probe end 30.

The distance is preferably selected based on the depth of the target 12 relative to the bone surface 16. As will be apparent to one of ordinary skill in the art, for a deep target, the distance will be relatively large. In contrast, the distance will be relatively small for a more superficial target. As will be readily apparent to one of ordinary skill in the art, the target depth will vary in keeping with the individual patient's anatomy and the surgical techniques being applied.

The probe depth limiter 44 is preferably immovably fixed relative to the shaft 26, such that each probe 24 is configured for use only in applications for which the predetermined limiting distance is suitable. However, it is permissible according to some aspects of the present invention for a longitudinally or axially shiftable depth limiter to be provided. Such an adjustable depth limiter would preferably be shiftable along the shaft to enable the longitudinal insertion distance to be set in accordance with the particular surgical need. Adjustment might be by any means known in the art, including but not limited to friction-resisted sliding or rotation along slanted screw threads (and consequent longitudinal shifting).

The probe depth limiter 44 preferably extends at least substantially continuously circumferentially to be generally toroidal or disc-like in form. Furthermore, as noted previously, the probe depth limiter 44 is preferably disposed orthogonally relative to a local portion of the shaft 26. However, alternative geometries and relative dispositions are permissible according to some aspects of the present invention. For instance, the depth limiter could be oriented at an angle such that a leading edge thereof is spaced from the distal end a different distance than a trailing edge, or the depth limiter could extend toward or away from the distal end so as to define an oblique angle between the depth limiter and the shaft. Yet further, as will be discussed in greater detail below with respect to an alternative embodiment of the present invention, the depth limiter could instead comprises a plurality of arcuately spaced apart, generally radially extending prongs.

In addition to being immovably fixed relative to the shaft 26, the probe depth limiter 44 is preferably itself generally rigid and immovable. It is permissible according to some aspects of the present invention, however, for the depth limiter to alternatively be at least in part flexible and/or deployable. For instance, the depth limiter could alternatively be configured to be shiftable between a retracted position enabling more streamlined insertion of the probe and a deployed position restricting further insertion of the probe into the bone.

The probe depth limiter 44 is preferably integrally formed with the shaft 26, although a discrete depth limiter fixed to the shaft by means of fasteners, adhesives, latches, friction, etc. may alternatively be provided.

It is also permissible according to some aspects of the present invention for the probe depth limiter to be omitted entirely.

FIG. 6 illustrates the trochar 20 of the system 10. The trochar 20 is configured to cut and/or penetrate into the bone 14 (e.g., a vertebra V or patella P, as discussed above) and/or surrounding tissues to form an access channel 46 to or to a location in close proximity to the target 12 prior to insertion of the probe 24.

The trochar 20 as illustrated includes a proximal trochar end 48, a distal trochar end 50 spaced from the proximal trochar end 48, and a main trochar body 52 extending between and interconnecting the proximal trochar end 48 and the distal trochar end 50. Preferably, the trochar 20 extends generally longitudinally, such that the distal trochar end 50 is spaced longitudinally from the proximal trochar end 48.

The proximal trochar end 48 preferably includes a trochar handle 54 for manual insertion or impaction (e.g., via receipt of compressive forces as from hammering, etc.).

The distal trochar end 50 preferably includes a cutting edge 56. The cutting edge 56 may be conical and comprise a sharp point 56a, as illustrated, or be configured in any other manner known in the art and suited for the particular application. For instance, the cutting edge could additionally or alternatively comprise a razor edge, a serrated edge, and/or drill threads.

Similar to the probe 24, the trochar 20 preferably includes a trochar depth limiter 58 configured to prevent over-insertion of the trochar 20 into the bone 14. The trochar depth limiter 58 preferably projects generally orthogonally relative to a longitudinal axis of the trochar 20 and is spaced a predetermined longitudinal distance from the distal trochar end 50.

The distance is selected based on the depth of the target 12 relative to a biological surface, such as the bone surface 16, through which access to the target 12 is accomplished. Furthermore, the distance is preferably the same as the distance associated with the probe depth limiter 44. However, the distances may vary if desired based on the particular application.

The trochar depth limiter 58 is preferably immovably fixed relative to the trochar 20, extends at least substantially continuously circumferentially to be generally toroidal or disc-like in form, and is generally rigid and inflexible. Yet further, the trochar depth limiter 58 is preferably integrally formed with the trochar 20.

It is noted however, than any of the alternative embodiments or features described above with respect to the probe depth limiter 44 are applicable to the trochar depth limiter 58. It is also permissible according to some aspects of the present invention for the trochar depth limiter to be omitted entirely.

As illustrated, the trochar 20 is preferably shaped to at least substantially correspond to the shape of the probe 24. For instance, in the preferred embodiment illustrated in FIGS. 4 and 5, the probe 24 is at least substantially straight. The corresponding trochar 20, as shown in FIG. 6, is therefore likewise at least substantially straight such that the channel 46 to the target 12 is at least substantially straight. Dissimilar shapes are permissible in some embodiments, however.

Preferably, the channel 46 formed by the trochar 20 is dimensioned so as to enable smooth insertion of at least the distal probe end 30 of the probe 24 therethrough, without being unduly large and thus prone to ingress of contaminants.

The trochar 20 preferably presents an at least substantially constant cross-sectional shape and size. More particularly, the trochar 20 preferably presents constant-diameter circular cross-sections. It is permissible according to some aspects of the present invention, however, for the trochar to present a non-circular cross-section. For instance, the trochar might be in the form of a rectangular prism and present a square cross-section. Furthermore, it is permissible according to some aspects of the present invention for the cross-sectional shape to vary axially or longitudinally. Yet further, the cross-sectional dimensions may vary, either for a constant cross-sectional shape or for embodiments featuring multiple cross-sectional shapes.

In a preferred embodiment, similarly to the shaft 26, the trochar 20 has a longitudinal dimension (i.e., a length) between about 20 cm and about 40 cm. More preferably, the trochar 20 has a longitudinal dimension of between about 25 cm and about 35 cm. Furthermore, the trochar 20 preferably has a maximum cross-sectional dimension (e.g., a diameter) of between about 1 mm to about 5 mm.

As noted above, in the preferred embodiment illustrated in FIG. 4, the shaft 26 comprises an electrically conductive material. It is therefore preferable that the system 10 further comprise the electrically insulative sleeve or sheath 22 for use with the probe 24.

The sheath 22 preferably guides the probe 24 to the target 12 so as to be in direct contact therewith or to a space in close proximity to the target 12 (close proximity meaning within a distance from which activation of the device will have the desired therapeutic effect on the target) such that the probe 24 engages the target, while at least substantially preventing the probe 24 from directly abutting or contacting surrounding biological structures. Most preferably, as illustrated, the probe 24 engages the target 12 by directly contacting the target 12, while completely avoiding contact with surrounding biological structures.

More particularly, the sheath 22 preferably includes a proximal sheath end 60, a distal sheath end 62 spaced from the proximal sheath end 60, and a main sheath body 64 extending between and interconnecting the proximal sheath end 60 and the distal sheath end 62. Preferably, the sheath 22 extends generally longitudinally, such that the distal sheath end 62 is spaced longitudinally from the proximal sheath end 60.

The sheath 22 further preferably comprises a sheath handle 66 to increase the ease of maneuverability of the sheath 22.

The sheath 22 further preferably defines a lumen 68 extending through the proximal sheath end 60, the main sheath body 64, and the distal sheath end 62. The lumen 68 is preferably sized to allow smooth passage of the probe 24 therethrough. Such smooth passage may be enabled by dimensional disparities between the probe 24 and the lumen 68, the use of probe and sheath materials having a low coefficient of friction relative to each other, and/or the use of lubricants.

In addition to preventing direct contact of the probe 24 with surrounding biological structures, the sheath 22 also preferably prevents transmission of electricity to surrounding biological structures. That is, the sheath 22 is preferably at least in part formed of an electrically insulative material so as to at least substantially prevent transmission of electricity from the probe 24 through the sheath 22 and into the patient.

Although any one or more of variety of sheath materials are permissible, plastic, rubber, and ceramic are preferred materials.

The sheath 22 also preferably provides at least some degree of thermal insulation between the main probe body 32 of the shaft 26 and the surrounding biological structures. The degree of thermal insulation required will vary according to the type of probe (e.g., thermal, electrocautery, or chemical) being used. For instance, an electrocautery probe 24, as illustrated, will generate heat due to resistance to the flow of electricity through the shaft 26.

The sheath 22 is preferably shaped to at least substantially correspond to the shape of the probe 24. For instance, in the preferred embodiment illustrated FIGS. 4 and 5, the probe 24 is at least substantially straight. The corresponding sheath 22 is therefore likewise at least substantially straight. However, dissimilar shapes are permissible in some embodiments.

The distal sheath end 62 may be configured in any manner suitable to the particular application. As illustrated, for instance, the distal sheath end 62 presents a flat edge 70 well suited for both stabilization and anti-slip purposes (e.g., against the outer surface 16 of the bone 14 after insertion of the sheath 22). Provision of a serrated edge would provide increased grip and anti-slip properties relative to the flat edge, while a pointed edge might also provide some degree of steadying assistance.

The sheath 22 may comprise an at least substantially rigid or at least substantially flexible material as optimal for the chosen application. For instance, the sheath might comprise a resiliently deformable material configured to expand or contract in response to the passage of the probe therethrough or instead be rigid in formation so as to provide a high-strength barrier around the probe.

Although the sheath 22 is preferably provided primarily or solely to guide the probe 24 to the target 12 or a space in close proximity thereto, the sheath 22 may alternatively be configured to additionally form the channel 46 to or nearly to the target (as described above with respect to the trochar 20). That is, the sheath may alternatively be configured similarly to the trochar 20, so as to form the channel 46 through bone and/or other biological structures (e.g., skin, fat, etc.) for access to the target or a space in close proximity thereto, in addition to thereafter guiding the probe to the target. In such a case, it will be apparent to one of ordinary skill in the art that a rigid sheath is preferred. Furthermore, it will be apparent to one of ordinary skill in the art that features described above with respect to the preferred trochar or alternatives thereto may also be applicable to the sheath. For instance, the sheath could be provided with a depth limiter to prevent over-insertion and the potential for accompanying tissue damage, and the configuration of the distal end of the sheath (e.g., serrated, pointed, threaded) etc. could be determined based on the desired channel-forming capabilities.

It is also noted that, in such a case, inclusion of a trochar in the system would potentially become unnecessary and redundant. Use of both a sheath and a trochar in formation of the channel, however, is nonetheless permissible. For instance, a trochar could be provided for formation of a pilot channel to be enlarged by the sheath, or a trochar could form a superficial portion of a channel with a sheath subsequently forming a deep portion of the channel.

Similarly, the probe could, in an alternative embodiment, be configured to in whole or in part form the channel. In such a case, it is noted that features described above with respect to the preferred trochar or sheath may also be applicable to the probe.

It is also noted that, in such a case, inclusion of a trochar in the system would potentially become unnecessary and redundant. As noted above with respect to the trochar, however, use of both a trochar and a probe (or a trochar, a sheath, and a probe) in formation of the channel is nonetheless permissible.

Yet further, use of any three (3) or more elements (e.g., a probe, one or more sheaths, and one or more trochars) is also permissible. For instance, a first sheath may be provided for channel formation purposes, while a second sheath is provided for steadying and protective purposes.

It is also permissible according to some aspects of the present invention for an entirely separate device, such as a drill or other sort of boring system, to be used to form the channel in whole or in part. Furthermore, any sort of suitable material removal technique, including but not limited to circular cutting, drilling motion, or direct puncture may be used, whether by the tools described explicitly herein or others known in the art.

In a preferred method of use of the system 10, the trochar 20 is first inserted into the bone 14 at an insertion location 72, distal trochar end 50 first, to form the bore, passageway, or channel 46 to or in close proximity to the target 12. The trochar depth limiter 58 preferably aids in achieving an appropriate insertion depth via abutment against the outer surface 16 of the bone 14.

The trochar 20 is then removed from the channel 46, and the sheath 22 is inserted, distal sheath end 62 first into the already formed channel 46.

The probe 24 is then inserted through the lumen 68 of the sheath 22, distal probe end 30 first, until the tip 42 is in contact with or in close proximity to the target 12.

The probe 24 is then activated, such that the electrode 36 cauterizes the target 12. More particularly, an electrical current from the power source (not shown) travels through the shaft 26 and the tip 42. Resistance to the electrical current elevates the temperature of the tip 42 such that the target 12 is ablated by the heat generated by the tip 42.

The probe 24 and the sheath 22 are then removed from the channel 46 and, more broadly, from the patient.

As will be apparent to one of ordinary skill in the art, prior to boring of the channel 46 and subsequent insertion of the sheath 22 and probe 24 thereinto, it will be necessary either to maneuver or navigate the trochar 20, the sheath 22, and/or the probe 24 through biological matter adjacent the bone 14 or to remove or shift such biological matter to enable direct access to the bone 14.

For instance, a percutaneous method might be implemented in which the trochar, the sheath, and the probe extend through a puncture in the subject's skin and are navigated through biological matter disposed between the puncture and the insertion location of the bone.

Alternatively, the method might be a secondary method to a primary surgical technique, wherein the entry location has been previously exposed due to prior opening of the skin and shifting of adjacent biological matter at least in part associated with the primary surgical technique. For instance, the method might be implemented before, during, or after a broader surgical repair of the spine (e.g., a vertebral fracture repair, spinal fixation, or tumor removal), wherein at least a portion of the patient's spine must be exposed for the primary surgery.

It is also noted that, although the method described herein is suitable for treatment of existing pain, such methodology may also be used preventively. For instance, the target may be ablated before, during, or after a primary surgery as a prophylactic measure against subsequent post-surgical pain.

Furthermore, is noted that proper positioning and use of the trochar 20, the probe 24, and/or the sheath 22 may be accomplished with the aid of any one or more of a variety of devices known in the surgical arts. For instance, the location at which the channel 46 should be formed may be indicated by use of computer tomography (CT), fluoroscopy, or any other device or instrument known to persons skilled in the art.

FIGS. 9-11 illustrate a second probe assembly embodiment. It is initially noted that, with certain exceptions to be discussed in detail below, many of the elements of the probe assembly 110 of the second embodiment are the same as or very similar to those described in detail above in relation to the probe assembly 18 of the first embodiment. Therefore, for the sake of brevity and clarity, redundant descriptions and numbering will be generally avoided here. Unless otherwise specified, the detailed descriptions of the elements presented above with respect to the first embodiment should therefore be understood to apply at least generally to the second embodiment, as well.

Similar to the probe assembly 18 of the first preferred embodiment, the probe assembly 110 of the second preferred embodiment comprises a probe 112 that includes an at least substantially straight shaft 114. The shaft 114 includes a proximal probe end 116, a distal probe end 118, and a main probe body 120 extending between and interconnecting the proximal probe end 116 and the distal probe end 118.

The shaft 114 also similarly comprises an electrically conductive material. However, in contrast to the probe 24 of the first preferred embodiment, which is configured for use in conjunction with the electrically insulative sheath 22, the probe 112 of the second preferred embodiment includes an electrically insulative covering 122 extending at least substantially over the main probe body 120. The covering 122 is preferably overmolded or powder coated onto the shaft 114, although other covering types are permissible.

Although use of a sheath in conjunction with the probe 112 for electrically insulative purposes is not required due to the presence of the covering 122, a sheath as describe above with regard to the sheath 22 may nonetheless be used. Furthermore, a trochar as described above with respect to the trochar 20 may also be used.

Also in contrast to the probe 24 of the first preferred embodiment, the probe 112 of the second preferred embodiment includes a blunt, rounded tip 124 at the distal probe end 118.

Furthermore, the probe 112 includes a unipolar electrode 126, in contrast to the bipolar electrode 36 of the probe 24.

Yet further, the probe 112 includes a plurality of temperature sensors 128 dispersed along the distal probe end 118. More particularly, in a preferred embodiment, as illustrated, the temperature sensors 128 are arranged in a pair of diametrically opposed, longitudinally extending sets 130 and 132.

The temperature sensors may be alternatively arranged, however. For instance, the sensors might be arranged to form one or more circumferentially extending rings about the probe, to be randomly distributed, to form a pattern, to extend beyond the distal probe end (e.g., onto the main probe body), to be positioned only in immediate proximity to the tip or the electrode, etc.

The temperature sensors 128 are preferably configured to enable avoidance of unintentional heating and/or cooling of non-target structures to temperatures greater than a chosen threshold temperature.

However, it is also permissible for one or more of the sensors, such as the sensors nearest the target after insertion of the probe, to be configured to detect the temperature proximate the target to ensure the desired temperature effect is achieved. For instance, the temperature sensors might be configured to assist in ensuring that a temperature of about 80° C. is maintained at or near the target for five (5) to seven (7) minutes. In such an embodiment, it is permissible and in some cases preferable for the temperature sensors to be associated with an automated control system that provides input to the probe (e.g., increased current, for instance, to generate more resistance-produced heat) in response to temperature sensor feedback.

In addition to the above, the probe 112 of the second preferred embodiment is provided with a depth limiter 134. In contrast to the circumferentially continuous probe depth limiter 44 of the first preferred embodiment, the depth limiter 134 of the second preferred embodiment preferably comprises a plurality of evenly arcuately spaced apart, generally radially extending prongs 136. Uneven spacing, alternative extension direction, and other variations are permissible, however, as are those variations described above with respect to the probe depth limiter 44 of the first preferred embodiment.

The generally straight probes 24 and 112 of FIGS. 4-5 and 9-11, respectively, are well-suited for use in ablation of certain target types. However, as discussed in greater detail below, a probe including one or more bends or turns is in some cases better suited for accessing a given target due to, for instance, the presence of an obstruction that, if damage to the obstruction is to be avoided, results in restrictions on the maneuverability of system components.

In keeping with the above, FIGS. 12-16 illustrate third through seventh preferred embodiments of the present invention. It is initially noted that, with certain exceptions to be discussed in detail below, many of the elements of the probe 210 of the third embodiment, the probe 310 of the fourth embodiment, the probe 410 of the fifth embodiment, the probe 510 of the sixth embodiment, and the probe 610 of the seventh embodiment are the same as or very similar to each other as well as to those probes described in detail above. Therefore, for the sake of brevity and clarity, redundant descriptions and numbering will be generally avoided here. Unless otherwise specified, the detailed descriptions of the elements presented above with respect to the first and/or second embodiments and below with respect to additional embodiments should therefore be understood to apply at least generally to the later-described embodiments, as well.

Turning now to FIG. 12, the probe 210 of the third preferred embodiment comprises a shaft 212. The shaft 212 includes a proximal probe end (not shown), a distal probe end 216 spaced from the proximal probe end (not shown), and a main probe body 218 extending between and interconnecting the proximal probe end (not shown) and the distal probe end 216. Preferably, the shaft 212 extends generally longitudinally, such that the distal probe end 216 is spaced longitudinally from the proximal probe end (not shown).

However, in contrast to main probe bodies 32 and 120 of the first and second preferred embodiments, the main probe body 218 includes an obstruction-avoidance portion 220. The obstruction-avoidance portion 220 is configured such that incidental damage to an obstruction or sensitive biological structure 222 by the shaft 212 is at least in part avoided prior to or during treatment of a target 224 in a bone 226.

The sensitive biological structure may be any biological structure disposed to or prone to damage during the course of the treatment method. For instance, the sensitive biological structure might be a fluid-filled structure (e.g., a vessel, a duct, or dura mater), a component of the alimentary canal, or a component of the lymphatic system.

Incidental damage to the sensitive biological structure includes but is not limited to thermal damage to the sensitive biological structure and prolonged retraction of the sensitive biological structure.

The obstruction-avoidance portion 220 preferably includes at least substantially straight proximal and distal shaft segments 228 and 230, respectively, defining an angle therebetween at an intersection 232.

The proximal shaft segment 228 preferably extends generally orthogonally relative to an outer surface 226a of the bone 226 and extends alongside or adjacent the sensitive biological structure 222.

The angle defined by the proximal and distal shaft segments 228 and 230 is most preferably an obtuse angle, although acute and/or right angles are permissible according to some aspects of the present invention. More particularly, the angle defined by the proximal and distal shaft segments 228 and 230 is preferably between about 105° and about 175°. More preferably, the angle defined by the proximal and distal shaft segments 228 and 230 is between about 120° and about 160°.

Thus, the distal shaft segment 230 preferably extends obliquely relative the bone surface 226a and, more particularly, preferably forms an acute angle therewith. Furthermore, in some instances, the distal shaft segment 230 is preferably positioned at least in part directly below the sensitive biological structure 222.

Preferably, the distal shaft segment 230 abuts or is at least in part coextensive with the distal probe end 216, such that the shaft 212 is at least substantially straight from the distal probe end 216 to the angle. Furthermore, the angle is preferably defined between about 1 mm and about 35 mm from the distal probe end 216. More preferably, the angle is defined between about 5 mm and about 30 mm from the distal probe end 216. However, it will be readily apparent to one of ordinary skill in the art that the optimal angle and positioning thereof will be dependent on the particular surgical technique to be used and the anatomy of the particular patient.

Although it is preferred that the proximal shaft segment 228 and the distal shaft segment 230 are each at least substantially straight, deviations from such preferred extension are permissible according to some aspects of the present invention.

In a preferred embodiment, as illustrated, the intersection 232 of the proximal shaft segment and the distal shaft segment defines a rounded corner 234. It is permissible, however, for a sharp corner to instead be defined.

As also shown in FIG. 12, a depth limiter 236 is preferably positioned adjacent and just proximal to the intersection 232.

Turning now to FIG. 13, the probe 310 of the fourth preferred embodiment comprises a shaft 312. The shaft 312 includes a proximal probe end (not shown), a distal probe end 316 spaced from the proximal probe end (not shown), and a main probe body 318 extending between and interconnecting the proximal probe end (not shown) and the distal probe end 316. Preferably, the shaft 312 extends generally longitudinally, such that the distal probe end 316 is spaced longitudinally from the proximal probe end (not shown).

The main probe body 318 includes an obstruction-avoidance portion 320 configured such that incidental damage to a sensitive biological structure 322 by the shaft 312 is at least in part avoided prior to or during treatment of a target 324 in a bone 326.

More particularly, the obstruction-avoidance portion 320 preferably includes a curved bend 328. The curved bend 328 preferably abuts or is at least in part coextensive with the distal probe end 316.

Furthermore, the curved bend 328 preferably presents a generally smooth curvature and, more particularly, extends at least in part along an arc of a circle. However, irregular and/or entirely non-circular curves are permissible according to some aspects of the present invention. For instance, the curved bend might instead extend along a parabolic trajectory.

Turning now to FIG. 14, the probe 410 of the fifth preferred embodiment comprises a shaft 412. The shaft 412 includes a proximal probe end (not shown), a distal probe end 416 spaced from the proximal probe end (not shown), and a main probe body 418 extending between and interconnecting the proximal probe end (not shown) and the distal probe end 416. Preferably, the shaft 412 extends generally longitudinally, such that the distal probe end 416 is spaced longitudinally from the proximal probe end (not shown).

The main probe body 418 includes an obstruction-avoidance portion 420 configured such that incidental damage to a sensitive biological structure 422 by the shaft 412 is at least in part avoided prior to or during treatment of a target 424 in a bone 426.

More particularly, the obstruction-avoidance portion 420 preferably includes a proximal section 428, a distal section 430 transversely offset relative to the proximal section 428, and an intermediate section 432 extending generally laterally or transversely between and interconnecting the proximal and distal sections 428 and 430, respectively. The proximal section 428 and the intermediate section 432 preferably define a proximal bend 434. Similarly, the intermediate section 432 and the distal section 430 preferably define a distal bend 436.

The proximal and distal bends 434 and 436, respectively, are preferably generally oppositely oriented. In other words, whereas one of the bends 434,436 is concave in a first direction, the other of the bends 434,436 is concave in an at least substantially opposite direction.

As shown in FIG. 14, the proximal bend 434 is preferably configured to circumvent the sensitive biological structure 422. More particularly, the proximal section 428 and the intermediate section 432 preferably each extend alongside or adjacent the sensitive biological structure 422. Furthermore, the intermediate section 432 preferably extends generally parallel to an outer surface 426a of the bone 426. The distal section 430 preferably penetrates the bone 426.

Preferably, the proximal section 428 and the distal section 430 are parallel to each other. Yet further, the proximal section 428 and the distal section 430 preferably extend at least substantially orthogonally relative to an outer surface 426a of the bone 426. Thus, the proximal section 428 and the distal section 430 are preferably at least substantially orthogonal to the intermediate section 232.

Preferably, the distal section 430 extends at least in part directly below the sensitive biological structure 422.

Preferably, the proximal, distal, and intermediate sections 428, 430, and 432, respectively are each at least substantially straight, such that the proximal bend 434 defines a proximal angle at a proximal intersection 438 and the distal bend 436 defines a distal angle at a distal intersection 440. Most preferably, with respect to the fifth preferred embodiment and a noted briefly above, the proximal and distal angles are right angles. Alternate configurations are permissible, however, and are discussed in detail below.

The intermediate section 432 is preferably spaced a predetermined longitudinal distance from the distal probe end 416. More particularly, the intermediate section 432 is preferably spaced a distance between about 1 mm and about 35 mm from the distal probe end 416. More preferably, the intermediate section 432 is preferably spaced a distance between about 5 mm and about 30 mm from the distal probe end 416.

As shown in FIG. 15, the probe 510 of the sixth preferred embodiment comprises a shaft 512. The shaft 512 includes a proximal probe end (not shown), a distal probe end 516 spaced from the proximal probe end (not shown), and a main probe body 518 extending between and interconnecting the proximal probe end (not shown) and the distal probe end 516. Preferably, the shaft 512 extends generally longitudinally, such that the distal probe end 516 is spaced longitudinally from the proximal probe end (not shown).

Similar to the probe 410 of the fifth preferred embodiment, the probe 510 of the sixth preferred embodiment includes a main probe body 518 that includes an obstruction-avoidance portion 520. The obstruction-avoidance portion 520 is configured such that incidental damage to a sensitive biological structure 522 by the shaft 512 is at least in part avoided prior to or during treatment of a target 524 in a bone 526.

More particularly, the obstruction-avoidance portion 520 preferably includes a proximal section 528 and a distal section 530 at least in part transversely offset relative to the proximal section 528. The obstruction-avoidance portion 520 further includes an intermediate section 532 extending between and interconnecting the proximal and distal sections 528 and 530, respectively. The proximal section 528 and the intermediate section 532 preferably define a proximal bend 534. Similarly, the intermediate section 532 and the distal section 530 preferably define a distal bend 536.

The proximal and distal bends 534 and 536, respectively, are preferably generally oppositely oriented. In other words, whereas one of the bends 534,536 is concave in a first direction, the other of the bends 534,536 is concave in an at least substantially opposite direction.

Preferably, the proximal, distal, and intermediate sections 528, 530, and 532, respectively are each at least substantially straight, such that the proximal bend 534 defines a proximal angle at a proximal intersection 538 and the distal bend 536 defines a distal angle at a distal intersection 540. Most preferably, with respect to the sixth preferred embodiment, the proximal and distal angles are obtuse angles. In a preferred embodiment, the proximal and distal angles are each between about 105° and about 175°. More preferably, the proximal and distal angles are each between about 120° and about 160°.

As shown in FIG. 15, the distal bend 536 is preferably configured to circumvent the sensitive biological structure 522. More particularly, the intermediate section 532 preferably extends alongside or adjacent the sensitive biological structure 522. The distal section 530 preferably penetrates the bone 526 and extends through the bone 526 at least in part directly below the sensitive biological structure 522.

The proximal section 528 and the distal section 530 are preferably parallel to each other. Yet further, the proximal section 528 and the distal section 530 preferably extend at least substantially obliquely relative to the surface 526a of the bone 526. The intermediate section 532 preferably extends generally orthogonally relative to the surface 526a of the bone 526.

A seventh preferred embodiment of the present invention is shown in FIG. 16, which illustrates a probe 610 comprising a shaft 612 that includes a proximal probe end (not shown), a distal probe end 616 spaced from the proximal probe end, and a main probe body 618 extending between and interconnecting the proximal probe end and the distal probe end 616. Preferably, the shaft 612 extends generally longitudinally, such that the distal probe end 616 is spaced longitudinally from the proximal probe end (not shown).

The probe 610 of the seventh preferred embodiment includes a main probe body 618 that includes an obstruction-avoidance portion 620. The obstruction-avoidance portion 620 is configured such that incidental damage to a sensitive biological structure 622 by the shaft 612 is at least in part avoided prior to or during treatment of a target 624 in a bone 626.

More particularly, the obstruction-avoidance portion 620 preferably includes a proximal section 628 and a distal section 630 transversely offset relative to the proximal section 628. The obstruction-avoidance portion 620 further includes an intermediate section 232 extending between and interconnecting the proximal and distal sections 628 and 630, respectively. The proximal section 628 and the intermediate section 232 preferably define a proximal bend 634. Similarly, the intermediate section 232 and the distal section 630 preferably define a distal bend 636.

The proximal and distal bends 634 and 636, respectively, are preferably generally oppositely oriented. In other words, whereas one of the bends 634,636 is concave in a first direction, the other of the bends 634,636 is concave in an at least substantially opposite direction.

Preferably, the proximal and distal sections 628 and 630, respectively, are each at least substantially curved, such that the obstruction-avoidance portion 620 is at least substantially S-shaped.

Most preferably, with respect to the seventh preferred embodiment, the proximal and distal sections 628 and 630 extend along smooth curves. Still more preferably, the proximal and distal sections 628 and 630 extend at least in part along arcs of circles. The intermediate section 232 preferably extends generally orthogonally relative to a surface 626a of the bone 626.

As will be apparent to one of ordinary skill in the art, the previously described third through seventh preferred embodiments of the present invention, each of which includes an obstruction-avoidance portion, are particularly well suited for surgical situations in which a sensitive biological structure prevents, obstructs, complicates, or otherwise lessens the efficacy of direct approaches to the target by use of straight probes like the probes 24 and 112 of the first and second preferred embodiments. That is, in a broad sense, provision of an obstruction-avoidance portion having geometric features as described above provides a practitioner greater flexibility in determining a spatial approach and, more broadly, a general methodology or technique (including both percutaneous and secondary methods and techniques), for engaging an obstructed target.

For instance, a variety of generally anterior approaches (e.g., to a basivertebral nerve of a vertebra) are enabled at least in part via provision of an obstruction-avoidance portion as described herein.

Anterior approaches may in some instances be the only generally safe approaches to a target. For instance, anterior approaches to a basivertebral nerve of a cervical vertebra are highly advantageous. Anterior approaches may also be particularly advantageous in some procedures associated with the thoracic spine.

In view of the above, FIG. 17 illustrates a vertebra 710 including a main body 712 and a plurality of processes 714. The main body 612 preferably defines a generally anterior face 716 of the vertebra 710. The processes 714 preferably cooperatively define a generally posterior face 716 of the vertebra 710.

The vertebra 710 also includes a basivertebral nerve 720.

Also shown in FIG. 17 is a probe 722 including a shaft 724 configured in a manner similar to any of the shafts 212, 312, 412, 512, and 612 of the third through seventh preferred embodiments described above. Among other things, for instance, the shaft 724 includes a distal end 726 defining a tip 728 that includes an electrode 730. Furthermore, the shaft 724 includes a depth limiter 732 and an obstruction-avoidance portion (not shown).

Broadly speaking, the probe 722 is suitable for use in ablating the basivertebral nerve 720 via a method including the steps of maneuvering the probe 722 to circumvent a sensitive biological structure (not shown), such that incidental damage thereto by the probe 722 is at least in part avoided during the course of the maneuvering; inserting the probe 722 into the generally anterior face 716 of the vertebra 710 in a generally anterior-to-posterior direction; navigating the probe through the vertebra 710 toward the basivertebral nerve 720; engaging the basivertebral nerve 720 with the distal end 726 of the probe 722; and activating the probe 722 such that the basivertebral nerve 720 is ablated.

It is particularly noted that generally anterior face as used above with respect to the vertebral face should be understood to refer to a face that at least in part is oriented anteriorly, although the face may in some instances be largely or even primarily transversely oriented (e.g., as shown at the insertion location of the probe 722).

Furthermore, a generally anterior-to-posterior direction should be understood to be one having a component thereof extending from anterior to posterior or vice versa, although the direction may in some instances be largely or even primarily transverse (e.g., as shown in FIG. 17).

The aforementioned steps may be performed in any order deemed appropriate to the particular application and, in some cases, may occur in whole or in part simultaneously. Preferably, however, maneuvering of the probe 722 to circumvent the sensitive biological structure is completed prior to engagement of the basivertebral nerve 720 and activation of the probe 722. Furthermore, it is preferred that insertion of the probe 722 into the vertebra 710 and subsequent navigation therethrough occurs prior to engagement of the basivertebral nerve 720 and activation of the probe 722. Yet further, engagement of the basivertebral nerve 720 preferably commences prior to or simultaneously with activation of the probe 722.

Preferably, the step of maneuvering the obstruction-avoidance portion includes the step of guiding the obstruction-avoidance portion relative to the sensitive biological structure such that the obstruction-avoidance portion circumvents the sensitive biological structure during at least activation of the probe 722. More preferably, the obstruction-avoidance portion circumvents the sensitive biological structure during the entirety of target engagement and probe activation.

Although the above description presents features of preferred embodiments of the present invention, other preferred embodiments may also be created in keeping with the principles of the invention. Furthermore, as noted previously, these other preferred embodiments may in some instances be realized through a combination of features compatible for use together despite having been presented independently as part of separate embodiments in the above description.

The preferred forms of the invention described above are to be used as illustration only and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention set forth in the following claims.

What is claimed is:

1. A method of ablating a nerve disposed within a vertebra of a patient, said vertebra including a main body and a plurality of processes, said main body of the vertebra presenting a generally anterior face, said method comprising the steps of:

(a) positioning a probe to circumvent a sensitive biological structure external to the vertebra, such that incidental damage by the probe to the sensitive biological structure is at least in part avoided during the course of said positioning;

(b) inserting the probe into the generally anterior face of the main body of the vertebra in a generally anterior-to-posterior direction;

(c) navigating the probe through the main body of the vertebra toward the nerve;
(d) engaging the nerve with a distal end of the probe; and
(e) activating the probe such that the nerve is ablated,
said probe comprising a unitary shaft,
said shaft including a proximal end, said distal end, and a main body extending between and interconnecting the proximal end and the distal end,
said proximal end, said distal end, and said main body of the shaft being integrally formed with one another,
said main body of the shaft integrally forming an obstruction-avoidance portion that circumvents the sensitive biological structure during at least steps (a) and (e),
said obstruction-avoidance portion comprising a rigid material such that the obstruction-avoidance portion maintains a single, constant shape during each of steps (a)-(e),
said obstruction-avoidance portion of the shaft including a proximal section, a distal section at least in part transversely offset relative to the proximal section, and an intermediate section extending between and interconnecting the proximal and distal sections,
said proximal section and said intermediate section defining a proximal bend,
said intermediate section and said distal section defining a distal bend oriented such that the proximal bend and the distal bend are generally oppositely oriented,
said proximal, distal, and intermediate sections each being at least substantially straight, such that said proximal bend defines a proximal angle and said distal bend defines a distal angle,
said proximal and distal angles being at least substantially right angles,
said proximal and distal sections extending generally orthogonally relative to the anterior face during at least steps (a) and (e),
said intermediate section extending generally parallel to the anterior face during at least steps (a) and (e),
said proximal and intermediate sections each extending alongside the sensitive biological structure during at least steps (a) and (e).

2. The method of claim 1, said distal end comprising an electrode,
step (e) comprising the step of supplying electricity to the electrode.

3. The method of claim 1, wherein step (a) is completed prior to commencement of step (e).

4. The method of claim 1, said nerve being a basivertebral nerve.

5. The method of claim 1,
said sensitive biological structure being selected from the group consisting of a fluid-filled structure, a component of the alimentary canal, a component of the lymphatic system, an artery, and a vein.

6. The method of claim 1,
said incidental damage including but not limited to thermal damage to and/or prolonged retraction of said sensitive biological structure.

7. The method of claim 1,
step (c) including the step of penetrating the main body by a distance of between about 5 mm and about 30 mm.

8. The method of claim 1,
said distal section extending at least substantially parallel to said proximal section.

9. A method of ablating a nerve disposed within a vertebra of a patient, said vertebra including a main body and a plurality of processes, said main body of the vertebra presenting a generally anterior face, said method comprising the steps of:
(a) positioning a probe to circumvent a sensitive biological structure external to the vertebra, such that incidental damage by the probe to the sensitive biological structure is at least in part avoided during the course of said positioning;
(b) inserting the probe into the generally anterior face of the main body of the vertebra in a generally anterior-to-posterior direction;
(c) navigating the probe through the main body of the vertebra toward the nerve;
(d) engaging the nerve with a distal end of the probe; and
(e) activating the probe such that the nerve is ablated,
said probe comprising a unitary shaft,
said shaft including a proximal end, said distal end, and a main body extending between and interconnecting the proximal end and the distal end,
said proximal end, said distal end, and said main body of the shaft being integrally formed with one another,
said main body of the shaft integrally forming an obstruction-avoidance portion that circumvents the sensitive biological structure during at least steps (a) and (e),
said obstruction-avoidance portion comprising a rigid material such that the obstruction-avoidance portion maintains a single, constant shape during each of steps (a)-(e),
said obstruction-avoidance portion of the shaft including a proximal section, a distal section at least in part transversely offset relative to the proximal section, and an intermediate section extending between and interconnecting the proximal and distal sections,
said proximal section and said intermediate section defining a proximal bend,
said intermediate section and said distal section defining a distal bend oriented such that the proximal bend and the distal bend are generally oppositely oriented,
said proximal, distal, and intermediate sections each being at least substantially straight, such that said proximal bend defines a proximal angle and said distal bend defines a distal angle,
said proximal and distal angles being at least substantially obtuse angles,
said intermediate section extending generally orthogonally relative to the anterior face during at least steps (a) and (e),
said proximal and distal sections extending generally obliquely relative to the anterior face during at least steps (a) and (e),
said intermediate section extending alongside the sensitive biological structure during at least steps (a) and (e).

10. The method of claim 9,
said proximal and distal angles each being between about 120 degrees and about 160 degrees.

11. The method of claim 9,
said distal section extending at least substantially parallel to said proximal section.

12. The method of claim 9,
said distal end comprising an electrode,
step (e) comprising the step of supplying electricity to the electrode.

13. The method of claim 9,
wherein step (a) is completed prior to commencement of step (e).

14. The method of claim 9,
said nerve being a basivertebral nerve.

15. The method of claim 9,
said sensitive biological structure being selected from the group consisting of a fluid-filled structure, a component of the alimentary canal, a component of the lymphatic system, an artery, and a vein.

16. The method of claim 9,
said incidental damage including but not limited to thermal damage to and/or prolonged retraction of said sensitive biological structure.

17. The method of claim 9,
step (c) including the step of penetrating the main body by a distance of between about 5 mm and about 30 mm.

18. A method of ablating a nerve disposed within a vertebra of a patient, said vertebra including a main body and a plurality of processes, said main body of the vertebra presenting a generally anterior face, said method comprising the steps of:
  (a) positioning a probe to circumvent a sensitive biological structure external to the vertebra, such that incidental damage by the probe to the sensitive biological structure is at least in part avoided during the course of said positioning;
  (b) inserting the probe into the generally anterior face of the main body of the vertebra in a generally anterior-to-posterior direction;
  (c) navigating the probe through the main body of the vertebra toward the nerve;
  (d) engaging the nerve with a distal end of the probe; and
  (e) activating the probe such that the nerve is ablated,
said probe comprising a unitary shaft,
said shaft including a proximal end, said distal end, and a main body extending between and interconnecting the proximal end and the distal end,
said proximal end, said distal end, and said main body of the shaft being integrally formed with one another,
said main body of the shaft integrally forming an obstruction-avoidance portion that circumvents the sensitive biological structure during at least steps (a) and (e),
said obstruction-avoidance portion comprising a rigid material such that the obstruction-avoidance portion maintains a single, constant shape during each of steps (a)-(e),
said obstruction-avoidance portion of the shaft including a proximal section, a distal section at least in part transversely offset relative to the proximal section, and an intermediate section extending between and interconnecting the proximal and distal sections,
said proximal section and said intermediate section defining a proximal bend,
said intermediate section and said distal section defining a distal bend oriented such that the proximal bend and the distal bend are generally oppositely oriented,
said proximal and distal sections being at least substantially curved, such that the obstruction-avoidance portion is at least substantially S-shaped,
said intermediate section extending generally orthogonally relative to the anterior face during at least steps (a) and (e),
said intermediate section extending alongside the sensitive biological structure during at least steps (a) and (e).

19. The method of claim 18,
said distal end comprising an electrode,
step (e) comprising the step of supplying electricity to the electrode.

20. The method of claim 18,
wherein step (a) is completed prior to commencement of step (e).

21. The method of claim 18,
said nerve being a basivertebral nerve.

22. The method of claim 18,
said sensitive biological structure being selected from the group consisting of a fluid-filled structure, a component of the alimentary canal, a component of the lymphatic system, an artery, and a vein.

23. The method of claim 18,
said incidental damage including but not limited to thermal damage to and/or prolonged retraction of said sensitive biological structure.

24. The method of claim 18,
step (c) including the step of penetrating the main body by a distance of between about 5 mm and about 30 mm.

* * * * *